United States Patent
Zhao et al.

(10) Patent No.: US 10,132,751 B2
(45) Date of Patent: Nov. 20, 2018

(54) METHOD AND DEVICE FOR DETECTING FLATNESS OF A FLUORESCENT WHEEL IN A LASER LIGHT SOURCE

(71) Applicants: HISENSE CO., LTD., South area of Qingdao (CN); Hisense USA Corp., Suwanee, GA (US); HISENSE INTERNATIONAL CO., LTD., Shandong (CN)

(72) Inventors: Fei Zhao, South area of Qingdao (CN); Xianrong Liu, South area of Qingdao (CN)

(73) Assignees: HISENSE CO., LTD., South Area of Qingdao (CN); HISENSE USA CORPORATION, Suwanee, GA (US); HISENSE INTERNATIONAL CO., LTD., Qingdao, Shandong (CN)

( * ) Notice: Subject to any disclaimer, the term of this patent is extended or adjusted under 35 U.S.C. 154(b) by 102 days.

(21) Appl. No.: 15/174,407

(22) Filed: Jun. 6, 2016

(65) Prior Publication Data
US 2017/0131205 A1    May 11, 2017

(30) Foreign Application Priority Data
Nov. 11, 2015    (CN) .......................... 2015 1 0767271

(51) Int. Cl.
G01N 21/64   (2006.01)
G01B 11/30   (2006.01)
H01S 3/22    (2006.01)

(52) U.S. Cl.
CPC ........... *G01N 21/64* (2013.01); *G01B 11/306* (2013.01); *H01S 3/2207* (2013.01)

(58) Field of Classification Search
CPC ...................................................... G01N 21/64
See application file for complete search history.

(56) References Cited

U.S. PATENT DOCUMENTS

| 2,641,957 A * | 6/1953 | Vandermeer ......... G01B 11/275 33/288 |
| 3,589,709 A * | 6/1971 | Hey ..................... G01B 11/043 493/10 |
| 2009/0033939 A1 | 2/2009 | Lin et al. |

(Continued)

FOREIGN PATENT DOCUMENTS

| CN | 101358840 A | 2/2009 |
| CN | 101501831 A | 8/2009 |

(Continued)

OTHER PUBLICATIONS

Office Action issued in corresponding Chinese Patent Application No. 20150767271.4, dated Aug. 17, 2017.

*Primary Examiner* — David Porta
*Assistant Examiner* — Jeremy S Valentiner
(74) *Attorney, Agent, or Firm* — McDermott Will & Emery LLP (57) ABSTRACT

An embodiment of the present disclosure discloses a method for detecting flatness of a fluorescent wheel in a laser light source, comprising: acquiring, during the rotation of a fluorescent wheel, a spot of laser light emitted by a laser reflected from a substrate of the fluorescent wheel; determining an inner diameter of the spot; and determining flatness of the fluorescent wheel according to the inner diameter of the spot.

21 Claims, 3 Drawing Sheets

(56) References Cited

U.S. PATENT DOCUMENTS

2010/0177953 A1 7/2010 Hayashi et al.
2014/0078475 A1* 3/2014 Masuda ................ G03B 21/14
                                                            353/84

FOREIGN PATENT DOCUMENTS

| CN | 202630932 U | 12/2012 |
| CN | 103759676 A | 4/2014 |
| CN | 104677315 A | 6/2015 |
| JP | S55-017443 A | 2/1980 |

* cited by examiner

Fig. 1

(Prior art)

METHOD AND DEVICE FOR DETECTING FLATNESS OF A FLUORESCENT WHEEL IN A LASER LIGHT SOURCE

CROSS-REFERENCE TO RELATED APPLICATIONS

The present application claims the priority of Chinese Patent Application 201510767271.4, titled "METHOD AND DEVICE FOR DETECTING FLATNESS OF A FLUORESCENT WHEEL IN A LASER LIGHT SOURCE", the entire of which is incorporated herein by reference.

FIELD OF TECHNOLOGY

The present disclosure relates to the technical field of laser light sources, and in particular to a method and device for detecting flatness of a fluorescent wheel in a laser light source.

BACKGROUND

The laser projection display technology has advantages of vivid color, high brightness, low cost and the like. A laser projection display system may be generally divided into three portions, i.e., a laser light source system, an optical-mechanical lighting system, and a lens imaging system.

Figure 1:
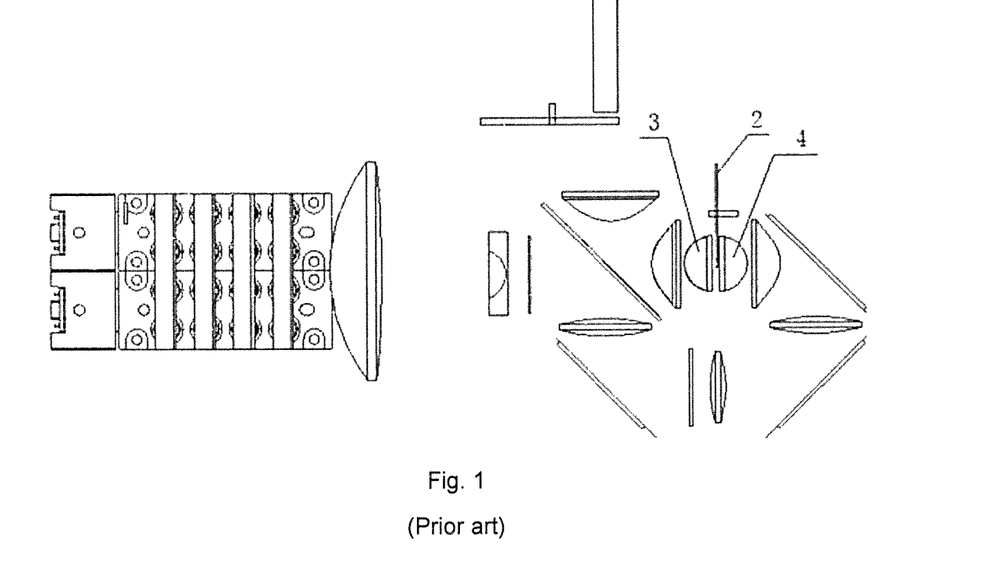
FIG. 1 is a schematic structure diagram of a laser light source in the prior art.

The laser light source system, as shown in FIG. 1, includes a laser, a fluorescent wheel 2, a lens, and other elements. The basic operation principle is as follows: after blue laser light emitted by a laser is irradiated onto a fluorescent wheel rotating at high speed, primary color light sources required by projection display are generated in timing sequence, and those primary color light sources are passed to the subsequent optical-mechanical lighting system and the lens imaging system to finally generate a colorful picture on the screen.

When in operation, the fluorescent wheel is always rotating at high speed. Due to a too small spacing between a front lens 3 and a rear lens 4 thereof, a wind cutting sound is generated during the rotation of the fluorescent wheel, and noise is thus caused. Furthermore, if the substrate of the fluorescent wheel becomes more out-of-flatness, the axial run-out during the rotation is more severe and the resulting noise is higher.

The machining process of fluorescent wheels is difficult to ensure excellent consistency of flatness of the produced substrates. There are always some fluorescent wheels unqualified in flatness. If such fluorescent wheel is assembled in a laser light source system, the finished machine product will generate high noise due to the out-of-flatness of this fluorescent wheel. Consequently, the finished machine product is unqualified. In order to deliver qualified finished machines, an existing approach is usually to detect noise of finished machines and reject unqualified products having high noise. To do this, it is necessary to establish a dedicated noise detection room where a person is specially assigned to detect noise of finished machines one by one. For those products having high noise rejected upon noise detection, it is necessary to replace their fluorescent wheel components. After the replacement, those products are subjected to noise detection again. This will be repeated until those products are qualified.

Obviously, this approach of rejecting fluorescent wheels unqualified in flatness by detecting noise of finished machines in the prior art increases the complexity of detection and decreases the production efficiency.

SUMMARY OF THE DISCLOSURE

An embodiment of the present disclosure provides a method for detecting flatness of a fluorescent wheel in a laser light source, including: acquiring, during the rotation of a fluorescent wheel, a spot of laser light emitted by a laser reflected from a substrate of the fluorescent wheel; determining an inner diameter of the spot; and determining flatness of the fluorescent wheel according to the inner diameter of the spot.

In addition, an embodiment of the present disclosure further provides a device for detecting flatness of a fluorescent wheel in a laser light source, including a fluorescent wheel, a laser, a spot receiving screen, a spot acquisition unit and a flatness detection unit; said laser is configured to emit laser light which is to be irradiated onto a wheel surface of the fluorescent wheel; said fluorescent wheel is configured to reflect, after receiving laser light emitted by the laser during the rotation, the laser light; said spot receiving screen is configured to form a spot in its plane after receiving the laser light reflected from the fluorescent wheel; said spot acquisition unit is configured to acquire the spot which is formed by reflecting the laser light emitted by said laser onto said spot receiving screen; and said flatness detection unit is configured to analyze an inner diameter of the spot, and determine flatness of the fluorescent wheel according to the inner diameter.

DETAILED DESCRIPTION OF THE PREFERRED EMBODIMENTS

To make the objectives, technical solutions and advantages of the present disclosure more clear, the present disclosure will be further described in detail as below with reference to the accompanying drawings. Apparently, the described embodiments are merely some but not all of embodiments of the present disclosure. All other embodiments made on the basis of the embodiments of the present disclosure by those skilled in the art without paying any creative effort shall be included in the protection scope of the present disclosure.

Embodiments of the present disclosure are aimed to provide a method and device for detecting flatness of a fluorescent wheel in a laser light source. By this method and device, instead of eliminating the influence of unqualified fluorescent wheels on a finished machine by detecting noise of the finished machine, the correspondence between the flatness of the fluorescent wheel and the noise of the finished machine is established according to test data, and according to the graph of the correspondence, by testing the diameter parameter of spots of the fluorescent wheels, the fluorescent wheels may be screened to select a fluorescent wheel enabling the noise of the finished machine to be qualified for production. In this way, it is unnecessary to detect the noise of every produced finished machine, so that the production efficiency is significantly improved while ensuring the quality of products. Compared with the way of detecting the noise of the finished machine adopted in the prior art, this approach in which only fluorescent wheels are screened can improve the production efficiency and save the production cost and resources.

The method by testing the diameter parameter of spots of the fluorescent wheels is based on the following. When a driving motor used for driving a fluorescent wheel rotates at high speed, the fluorescent wheel is driven to rotate at high speed. When a laser light beam is used to irradiate in a collimated manner onto a surface of the substrate of the fluorescent wheel (i.e., wheel surface), due to the high reflectivity of the fluorescent wheel, the incident laser light beam will be reflected. The reflected laser light beam is received by the spot receiving screen, and an irregular spot is formed on the spot receiving screen. Such an irregular spot is the result of the out-of-flatness of the substrate and the axial run-out of the fluorescent wheel during its rotation. Since the spot is formed during the rotation of the fluorescent wheel, and the laser light beam is irradiated onto the whole circle of the wheel surface of the fluorescent wheel during its rotation, due to the out-of-flatness of the substrate and the axial run-out of the fluorescent wheel, when the laser light beam is irradiated onto points on the wheel surface of the fluorescent wheel, the incident angles at those points will be different. Hence, after the laser light beam is reflected by the fluorescent wheel, those reflected laser light points form an irregular spot on the spot receiving screen. This shows that the irregularity of the spot indicates the flatness of the whole fluorescent wheel.

The out-of-flatness and axial run-out of the fluorescent wheel are main reasons that cause the noise of the finished machine. Hence, the concept of the embodiments of the present disclosure lies in that all fluorescent wheels to be used for production are tested, a corresponding spot of each fluorescent wheel is acquired, an inner diameter of each spot is determined, and then the flatness of the fluorescent wheel is determined according to the characteristic of the inner diameter of the spot. For example, a maximum inner diameter, an average inner diameter and a minimum inner diameter of each spot may be determined. A larger maximum inner diameter indicates larger change in flatness and axial run-out of a fluorescent wheel, as well as higher noise when such a fluorescent wheel is assembled in a finished machine. Hence, a maximum noise value allowed by the finished machine is set. By delimiting a maximum inner diameter, a ratio of the maximum inner diameter to an average inner diameter, or a ratio of the maximum inner diameter to a minimum inner diameter of a spot corresponding to this maximum noise value, when a fluorescent wheel having a spot less than the maximum inner diameter, the ratio of the maximum inner diameter to the average inner diameter, or the ratio of the maximum inner diameter to the minimum inner diameter is assembled in the finished machine, the noise of the finished machine meets the requirement on noise.

It is to be noted that, in the embodiments of the present disclosure, when the fluorescent wheel is driven to rotate at high speed, theoretically, the rotating surface of the fluorescent wheel should be in a plane perpendicular to the driving shaft. However, when the fluorescent wheel is unqualified in flatness, the rotating surface of the fluorescent wheel will be deviated from this plane. Hence, in the embodiments of the present disclosure, the flatness of the fluorescent wheel may refer to the degree of deviation of the rotating surface of the fluorescent wheel from the plane perpendicular to the driving shaft when the fluorescent wheel is driven to rotate at high speed.

Based on the foregoing, the technical solutions provided by the embodiments of the present disclosure will be described in detail with reference to the accompanying drawings.

Figure 2:
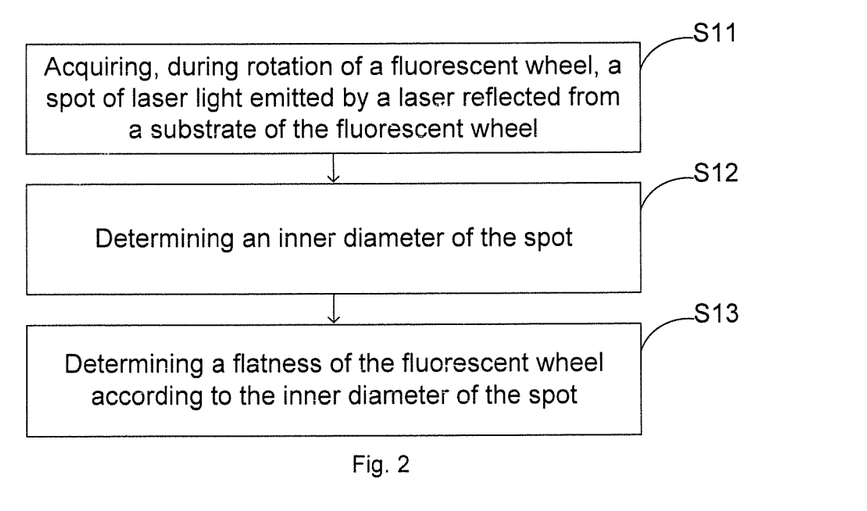
FIG. 2 is a flowchart of a method for detecting flatness of a fluorescent wheel in a laser light source according to an embodiment of the present disclosure.

In the flowchart as shown in FIG. 2, one embodiment of the present disclosure provides a method for detecting flatness of a fluorescent wheel in a laser light source, including the following steps:

S11: acquiring, during rotation of a fluorescent wheel, a spot of laser light emitted by a laser reflected from a substrate of the fluorescent wheel;

S12: determining an inner diameter of the spot; and

S13: determining a flatness of the fluorescent wheel according to the inner diameter of the spot.

In the method for detecting flatness of a fluorescent wheel in a laser light source according to the embodiment of the present disclosure, according to the correspondence between the flatness of the fluorescent wheel and the noise of the finished machine which shows that the noise of the finished machine is higher if the flatness is worse, a spot, formed by laser irradiating a laser light beam onto the wheel surface of the fluorescent wheel and then it being reflected from the wheel surface onto the spot receiving screen, is detected. When the fluorescent wheel is fully flat, the spot formed on the spot receiving screen should be theoretically one laser point. When the flatness of the fluorescent wheel is good, its corresponding spot should be a circular spot having a substantially identical inner diameter. Due to the presence of out-of-flatness or axial run-out of the fluorescent wheel, the spot thereof formed on the spot receiving screen is an irregular spot. Hence, the flatness of the fluorescent wheel may be determined by determining the inner diameter of the spot and according to the characteristic of the inner diameter of the spot.

Thus, the embodiment of the present disclosure provides a method for directly detecting flatness of a fluorescent wheel, by which fluorescent wheels unqualified in flatness are screened out so that a fluorescent wheel assembled in the finished machine generates noise lower than the allowable maximum noise. Compared with the method by detecting the noise of the finished machine adopted in the prior art, the method provided by the above embodiment may reject fluorescent wheels unqualified in flatness before assembling them in the finished machines, so that all produced finished machines meet the requirement on noise, without needing to establish a noise detection room, detect the noise of the finished machine, replace the fluorescent wheel for the finished machine unqualified in noise, or even detect the noise of the finished machine again after replacing the fluorescent wheel. Hence, the production efficiency may be improved.

Figure 3:
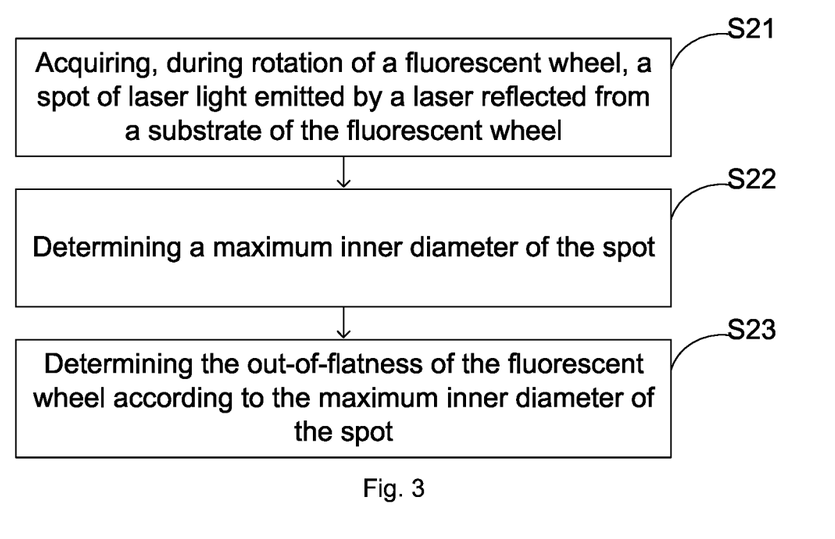
FIG. 3 is a flowchart of a method for detecting flatness of a fluorescent wheel in a laser light source according to another embodiment of the present disclosure.

Specifically, in the flowchart as shown in FIG. 3, another embodiment of the present disclosure provides a method for detecting flatness of a fluorescent wheel in a laser light source includes the following steps:

S21: Acquiring, during rotation of a fluorescent wheel, a spot of laser light emitted by a laser reflected from a substrate of the fluorescent wheel.

To make the acquired spot comprehensively reflect the flatness and axial run-out of the substrate of the whole fluorescent wheel, it is necessary to drive the fluorescent wheel to keep rotating during the test. In this way, the laser light emitted by the laser may be irradiated onto the whole circle of the wheel surface of the fluorescent wheel, and the acquired spot may really reflect the flatness and axial run-out of the whole fluorescent wheel.

The front surface or rear surface of the substrate of the fluorescent wheel is required to be a polished surface, or to be coated with a high-reflectivity layer. In this way, a clear edge of a spot formed by reflecting laser light emitted by a laser can be ensured. A clear edge facilitates the analysis and determination of the inner diameter of the spot.

Figure 4:
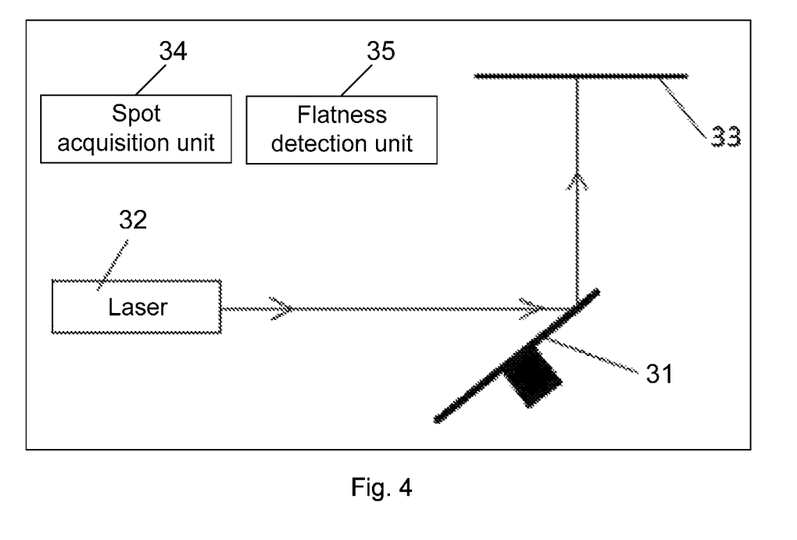
FIG. 4 is an architecture diagram of a device for detecting flatness of a fluorescent wheel in a laser light source according to an embodiment of the present disclosure.
Figure 5:
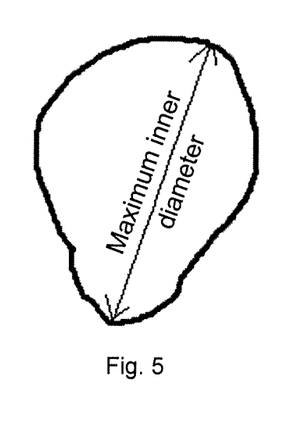
FIG. 5 is a schematic diagram of a spot when a respective spot of a fluorescent wheel is detected, according to one embodiment of the present disclosure.

The laser is placed on one side of the fluorescent wheel, and during the rotation of the fluorescent wheel, emits laser light which is to be irradiated onto the wheel surface of the fluorescent wheel. Before acquiring a spot, the incident angle of laser light emitted by the laser is controlled to be deviated from a normal line of the substrate and be less than 90°, that is, the incident angle of laser light is greater than 0° and less than 90°. For example, as shown in FIG. 4, the incident angle of laser light may be about 45°. In this case, due to the high reflectivity of the fluorescent wheel, after a laser light beam is irradiated onto the fluorescent wheel, the laser light beam is undoubtedly reflected at a certain angle. If the reflected laser light beam is received by a white spot receiving screen, the laser light beam forms an irregular spot on the receiving screen, as shown in FIG. 5. The irregularity of the spot indicates the presence of the out-of-flatness and axial run-out of the fluorescent wheel.

According to theory of noise, the closer to the peripheral region of the substrate of the fluorescent wheel, the greater influence on the noise of the assembled finished machine. Hence, preferably, before acquiring, during the rotation of a fluorescent wheel, a spot of laser light emitted by a laser reflected from a substrate of the fluorescent wheel, laser light emitted by the laser is controlled to be irradiated onto the peripheral region of the substrate of the fluorescent wheel.

It is to be noted that, when laser light is irradiated onto the front surface of the fluorescent wheel, since the outer diameter of the front surface of the fluorescent wheel is coated with fluorescent powder, the region having fluorescent powder should be bypassed when the laser is controlled to emit laser light.

S22: Determining a maximum inner diameter of the spot.

If the flatness of the fluorescent wheel is worse, the axial run-out is more severe, the spot is more irregular, and the change in inner diameter of the spot is greater. Accordingly, after the inner diameter of the spot is measured, a maximum inner diameter may be determined. This maximum inner diameter represents the worst flatness of the fluorescent wheel.

S23: Determining the out-of-flatness of the fluorescent wheel according to the maximum inner diameter of the spot.

Among a plurality of fluorescent wheels prepared to be used for production, a maximum inner diameter of each fluorescent wheel is acquired according to S21 and S22. In this case, among a plurality of spots, the spots are sorted from small to large according to their maximum inner diameters. A spot having a smaller maximum inner diameter shows that its corresponding fluorescent wheel has better flatness. While a spot having a larger maximum inner diameter shows that its corresponding fluorescent wheel has worse flatness.

Thus, the out-of-flatness of the fluorescent wheel may be determined according to the maximum inner diameter of the spot. Specifically, for each spot, it is judged whether the maximum inner diameter of the spot is less than or equal to a preset inner diameter value. If the maximum inner diameter of the spot is less than or equal to a preset inner diameter value, a corresponding fluorescent wheel is marked as qualified in flatness. If the maximum inner diameter of the spot is not less than or equal to a preset inner diameter value, a corresponding fluorescent wheel is marked as unqualified in flatness.

Herein, the preset inner diameter value is an empirical value or a statistical analysis value. It usually refers to the maximum inner diameter of a spot corresponding to a fluorescent wheel which, when assembled in a finished machine, generates noise equal to the upper limit of allowable noise for the finished machine.

The following description will be given by taking, as an example, a case in which N fluorescent wheels to be used for production are detected: acquiring N spots reflected, during the rotation of N fluorescent wheels, from respective substrates of the N fluorescent wheels, respectively; then, determining N maximum inner diameters of the N spots; then, assembling the N fluorescent wheels in N finished machines and detecting the noise of the N finished machines, and acquiring the noise generated by the N fluorescent wheels when assembled in the finished machines respectively; finally, determining said preset inner diameter value according to an upper limit of allowable noise. That is, an upper limit of noise allowed by the finished machines is defined. N noise decibel values are measured from the N finished machines, respectively. Among those fluorescent wheels, a fluorescent wheel, which is assembled in a finished machine generating noise lower than the upper limit of allowable noise, is qualified in flatness, and a corresponding spot has a maximum inner diameter less than the preset inner value; a fluorescent wheel, which is assembled in a finished machine generating noise higher than the upper limit of allowable noise, is unqualified in flatness, and a corresponding spot has a maximum inner diameter greater than the preset inner value; and for a fluorescent wheel which is assembled in a finished machine generating noise equal to the upper limit of allowable noise, a corresponding spot has a maximum inner diameter equal to the preset inner value.

In the foregoing, in the method for detecting flatness of a fluorescent wheel in a laser light source provided by the embodiment of the present disclosure, according to the correspondence between the flatness of the fluorescent wheel and the noise of the finished machine which shows that the noise of the finished machine is higher if the flatness is worse, a spot, formed by laser irradiating a laser light beam onto the wheel surface of the fluorescent wheel and then it being reflected from the wheel surface onto the spot receiving screen, is detected, and a maximum inner diameter of the spot is determined. A spot having a larger maximum inner diameter shows that a corresponding fluorescent wheel has worse flatness and a finished machine assembled with such a fluorescent wheel generates higher noise. Hence, screening out a fluorescent wheel corresponding to a spot having a maximum inner diameter greater than the preset inner diameter value is to screen out a fluorescent wheel which results in high noise of the finished machine due to its insufficient flatness.

For a desired fluorescent wheel having good flatness, its corresponding spot should be a circular spot having a substantially identical inner diameter. Due to the presence of out-of-flatness or axial run-out of the fluorescent wheel, the spot thereof formed on the spot receiving screen is an irregular spot. A worse flatness of the fluorescent wheel indicates larger change in inner diameter of the corresponding irregular spot. When it is set that a maximum inner diameter of a spot corresponding to the allowable maximum noise is the preset inner diameter value, the flatness of a fluorescent wheel corresponding to a spot having a maximum inner diameter less than or equal to the preset inner diameter value meets the requirement, and after assembling such a fluorescent wheel in a finished machine, the noise of the finished machine is less than or equal to the allowable maximum noise; and the flatness of a fluorescent wheel corresponding to a spot having a maximum inner diameter greater than the preset inner diameter value does not meet the requirement, and after assembling such a fluorescent wheel in a finished machine, the noise of the finished machine is greater than the allowable maximum noise.

Thus, fluorescent wheels unqualified in flatness are screened out, thereby ensuring that a fluorescent wheel generates in a finished machine, when assembled in the finished machine, noise less than or equal to the allowable maximum noise. Compared with the method by detecting the noise of the finished machine adopted in the prior art, the method provided by the embodiment of the present disclosure may reject fluorescent wheels unqualified in flatness before assembling them in the finished machine, so that all produced finished machines meet the requirement on noise, without needing to establish a noise detection room, detect the noise of the finished machine, replace the fluorescent wheel for the finished machine unqualified in noise, or even detect the noise of the finished machine again after replacing the fluorescent wheel. Hence, the production efficiency may be improved.

Alternatively, in another embodiment of the present disclosure, the out-of-flatness of the fluorescent wheel may be determined according to a ratio of the maximum inner diameter to the average inner diameter of the spot. That is, the above S22 and S23 may be replaced with following S32 and S33, respectively.

S32: Determining a maximum inner diameter and an average inner diameter of the spot.

During the detection, the fluorescent wheel rotates continuously, and its flatness usually changes continuously. The incident angles of laser light at points when the laser light is irradiated onto the whole circle of the wheel surface of the fluorescent wheel usually changes continuously. Correspondingly, the spot formed on the spot receiving screen is usually a closed curve.

If the flatness of the fluorescent wheel is worse, the axial run-out is more severe, the spot is more irregular, and the change in inner diameter of the spot is greater. Accordingly, after the inner diameter of the spot is measured, the worst flatness of the fluorescent wheel may be represented by the ratio of the maximum inner diameter to the average inner diameter of the spot.

S33: Determining the flatness of the fluorescent wheel according to the ratio of the maximum inner diameter to the average inner diameter of the spot.

Among a plurality of fluorescent wheels prepared to be used for production, a maximum inner diameter and an average inner diameter of each fluorescent wheel is acquired according to S21 and S32. In this case, among a plurality of spots, the spots are sorted from small to large, according to the ratio of the maximum inner diameter to the average inner diameter of each spot. A spot having a smaller ratio shows that a corresponding fluorescent wheel has better flatness. While a spot having a larger ratio shows that a corresponding fluorescent wheel has worse flatness.

Thus, the out-of-flatness of the fluorescent wheel may be determined according to the ratio of the maximum inner diameter to the average inner diameter of the spot. Specifically, for each spot, it is judged whether the ratio of the maximum inner diameter to the average inner diameter of the spot is less than or equal to a first preset ratio. If the ratio of the maximum inner diameter to the average inner diameter of the spot is less than or equal to a first preset ratio, a corresponding fluorescent wheel is marked as qualified in flatness. If the ratio of the maximum inner diameter to the average inner diameter of the spot is not less than or equal to a first preset ratio, a corresponding fluorescent wheel is marked as unqualified in flatness.

Herein, the first preset ratio is an empirical value or a statistical analysis value. It usually refers to the ratio of the maximum inner diameter to the average inner diameter of a spot corresponding to a fluorescent wheel which, when assembled in a finished machine, generates noise equal to the upper limit of allowable noise for the finished machine.

The following description will be given by taking, as an example, a case in which N fluorescent wheels to be used for production are detected: acquiring N spots reflected, during the rotation of N fluorescent wheels, from respective substrates of the N fluorescent wheels, respectively; then, determining N maximum inner diameters and N average inner diameters of the N spots; then, assembling the N fluorescent wheels in N finished machines and detecting the noise of the N finished machines, and acquiring the noise generated by the N fluorescent wheels when assembled in the finished machines respectively; finally, determining said first preset ratio according to an upper limit of allowable noise. That is, an upper limit of noise allowed by the finished machines is defined. N noise decibel values are measured from the N finished machines, respectively. Among those fluorescent wheels, a fluorescent wheel, which is assembled in a finished machine generating noise lower than the upper limit of allowable noise, is qualified in flatness, and a corresponding spot has a ratio of the maximum inner diameter to the average inner diameter less than the first preset ratio; a fluorescent wheel, which is assembled in a finished machine generating noise higher than the upper limit of allowable noise, is unqualified in flatness, and a corresponding spot has a ratio of the maximum inner diameter to the average inner diameter greater than the first preset ratio; and for a fluorescent wheel which is assembled in a finished machine generating noise equal to the upper limit of allowable noise, a corresponding spot has a ratio of the maximum inner diameter to the average inner diameter equal to the first preset ratio.

Alternatively, in still another embodiment of the present disclosure, the out-of-flatness of the fluorescent wheel may be determined according to a ratio of the maximum inner diameter to the minimum inner diameter of the spot. That is, the above S22 and S23 may be replaced with following S42 and S43, respectively.

S42: Determining a maximum inner diameter and a minimum inner diameter of the spot.

S43: Determining the flatness of the fluorescent wheel according to the ratio of the maximum inner diameter to the minimum inner diameter of the spot.

Specifically, S43 may include: for each spot, it is judged whether the ratio of the maximum inner diameter to the minimum inner diameter of the spot is less than or equal to a second preset ratio. If the ratio of the maximum inner diameter to the minimum inner diameter of the spot is less than or equal to a second preset ratio, a corresponding fluorescent wheel is marked as qualified in flatness. If the ratio of the maximum inner diameter to the minimum inner diameter of the spot is not less than or equal to a second preset ratio, a corresponding fluorescent wheel is marked as unqualified in flatness.

Herein, the second preset ratio is an empirical value or a statistical analysis value. It usually refers to the ratio of the maximum inner diameter to the minimum inner diameter of a spot corresponding to a fluorescent wheel which, when assembled in a finished machine, generates noise equal to the upper limit of allowable noise for the finished machine.

The following description will be given by taking, as an example, a case in which N fluorescent wheels to be used for production are detected: acquiring N spots reflected, during the rotation of N fluorescent wheels, from respective substrates of the N fluorescent wheels, respectively; then, determining N maximum inner diameters and N minimum inner diameters of the N spots; then, assembling the N fluorescent wheels in N finished machines and detecting the noise of the N finished machines, and acquiring the noise generated by the N fluorescent wheels which were assembled in the finished machines respectively; finally, determining said second preset ratio according to an upper limit of allowable noise. That is, an upper limit of noise allowed by the finished machines is defined. N noise decibel values are measured from the N finished machines, respectively. Among those fluorescent wheels, a fluorescent wheel, which is assembled in a finished machine generating noise lower than the upper limit of allowable noise, is qualified in flatness, and a corresponding spot has a ratio of the maximum inner diameter to the minimum inner diameter less than the second preset ratio; a fluorescent wheel, which is assembled in a finished machine generating noise higher than the upper limit of allowable noise, is unqualified in flatness, and a corresponding spot has a ratio of the maximum inner diameter to the minimum inner diameter greater than the second preset ratio; and for a fluorescent wheel which is assembled in a finished machine generating noise equal to the upper limit of allowable noise, a corresponding spot has a ratio of the maximum inner diameter to the minimum inner diameter equal to the second preset ratio.

In the embodiments of the present disclosure, the inner diameter of the spot may be measured according to the existing image processing methods. For example, image data of the spot is acquired by a sensor or image acquisition device, and the image data is recognized and analyzed to determine the inner diameter of the spot, for example, the maximum inner diameter, the average inner diameter or the minimum inner diameter; or, scales are marked on the spot receiving surface, and then the formed spot is analyzed after drawing its profile. The specific measurement method is not specifically limited in the embodiments of the present application.

As shown in FIG. 4, an embodiment of the present disclosure further provides a device for detecting flatness of a fluorescent wheel in a laser light source, including a fluorescent wheel 31, a laser 32, a spot receiving screen 33, a spot acquisition unit 34 and a flatness detection unit 35.

The laser 32 is configured to emit laser light which is to be irradiated onto the wheel surface of the fluorescent wheel 31; the fluorescent wheel 31 is configured to reflect, after receiving laser light emitted by the laser 32 during the rotation, the laser light; the spot receiving screen 33 is configured to form a spot in its plane after receiving the laser light reflected from the fluorescent wheel 31; the spot acquisition unit 34 is configured to acquire the spot of the laser light emitted by the laser 32 reflected onto the spot receiving screen 33; and the flatness detection unit 35 is configured to analyze an inner diameter of the spot, and determine flatness of the fluorescent wheel 31 according to the inner diameter.

The front surface or rear surface of the substrate of the fluorescent wheel is required to be a polished surface, or to be coated with a high-reflectivity layer. In this way, a clear edge of a spot formed by reflecting laser light emitted by a laser can be ensured. A clear edge facilitates the analysis and determination of the inner diameter of the spot.

As described in the above embodiments, the inner diameter of the spot indicates the flatness of the fluorescent wheel, and if the flatness is worse, the spot is more irregular. This device is used to acquire a spot, formed on the spot receiving screen 33, of a laser light beam emitted by a laser reflected during the rotation of the fluorescent wheel, and the flatness of the fluorescent wheel may be determined according to the measurement of the inner diameter of the spot. After a fluorescent wheel is assembled in a finished machine, higher noise of the finished machine indicates worse flatness of the fluorescent wheel. Hence, the noise of a corresponding finished machine may be known by measuring the flatness of the fluorescent wheel. Therefore, a step of obtaining the flatness of the fluorescent wheel by detecting the noise of the finished machine in the prior art is simplified as direct detection of the flatness of the fluorescent wheel, thereby saving the steps of detecting the noise of the finished machine and replacing the fluorescent wheel if it is unqualified upon detection. The production efficiency may be significantly improved.

In the embodiments of the present disclosure, the inner diameter of the spot may be analyzed according to the existing image processing methods. For example, the spot acquisition unit may be a sensor or image acquisition device, for example, a camera. The flatness detection unit may be arranged in a computer, specifically in a processor. For example, when image data of the spot is acquired by a spot acquisition unit, the image data is recognized and analyzed by the flatness detection unit arranged in the computer, and the flatness of the fluorescent wheel is determined according to the inner diameter.

Or, the inner diameter of the spot may be analyzed in a conventional way. For example, the spot acquisition unit may be a pen and a paper; and the flatness detection unit may be a length measurement tool, for example, a scale, a vernier caliper, a flexible rule or the like. For example, when a spot on the spot receiving screen is recorded in paper by a pen, the inner diameter of the spot is measured in a conventional measurement way, and the flatness of the fluorescent wheel is determined according to the inner diameter.

Specifically, in the embodiments of the present disclosure, the flatness of the fluorescent wheel is determined according to the maximum inner diameter, the ratio of the maximum inner diameter to the average inner diameter, or the ratio of the maximum inner diameter to the minimum inner diameter of the spot. Hence, correspondingly, the flatness detection unit may be specifically configured to determine a maximum inner diameter after analyzing the inner diameter of the spot, and determine the flatness of the fluorescent wheel according to the maximum inner diameter; or, determine a maximum inner diameter and an average inner diameter after analyzing the inner diameter of the spot, and determine the flatness of the fluorescent wheel according to a ratio of the maximum inner diameter to the average inner diameter of the spot; or, determine a maximum inner diameter and a minimum inner diameter after analyzing the inner diameter of the spot, and determine the flatness of the fluorescent wheel according to a ratio of the maximum inner diameter to the minimum inner diameter of the spot.

The flatness detection unit includes a flatness judgment module and a marking module.

When the flatness detection unit is specifically configured to determine a maximum inner diameter after analyzing the inner diameter of the spot, and determine the flatness of the fluorescent wheel according to the maximum inner diameter:

the flatness judgment module is configured to judge whether the maximum inner diameter of the spot is less than or equal to a preset inner diameter value; and the marking module is configured to: if the flatness judgment module judges that the maximum inner diameter of the spot is less than or equal to the preset inner diameter value, mark the fluorescent wheel as qualified in flatness, otherwise mark the fluorescent wheel as unqualified in flatness.

When the flatness detection unit is specifically configured to determine a maximum inner diameter and an average inner diameter after analyzing the inner diameter of the spot, and determine the flatness of the fluorescent wheel according to a ratio of the maximum inner diameter to the average inner diameter of the spot:

the flatness judgment module is configured to judge whether the ratio of the maximum inner diameter to the average inner diameter of the spot is less than or equal to a first preset ratio; and the marking module is configured to: if the flatness judgment module judges that the ratio of the maximum inner diameter to the average inner diameter of the spot is less than or equal to the first preset ratio, mark the fluorescent wheel as qualified in flatness, otherwise mark the fluorescent wheel as unqualified in flatness.

When the flatness detection unit is specifically configured to determine a maximum inner diameter and a minimum inner diameter after analyzing the inner diameter of the spot, and determine the flatness of the fluorescent wheel according to a ratio of the maximum inner diameter to the minimum inner diameter of the spot:

the flatness judgment module is configured to judge whether the ratio of the maximum inner diameter to the minimum inner diameter of the spot is less than or equal to a second preset ratio; and the marking module is configured to: if the flatness judgment module judges that the ratio of the maximum inner diameter to the minimum inner diameter of the spot is less than or equal to the second preset ratio, mark the fluorescent wheel as qualified in flatness, otherwise mark the fluorescent wheel as unqualified in flatness.

The laser 32 is preferably a He-Ne laser that can emit a collimated red laser light beam.

The spot receiving screen 33 is a white receiving screen or white wall.

For laser light sources employing the structure design as shown in FIG. 1, in the practical production, there may be cases in which some fluorescent wheels make finished machines unqualified in noise when assembled in finished machines. In one embodiment, in order to determine the correspondence between the fluorescent wheels and the noise of the finished machines, ten fluorescent wheels are selected as the samples for spot test by using the method and device as described in the above embodiments. Meanwhile, the ten fluorescent wheels are assembled in the finished machines for testing the noise of the finished machines. The results of tests are as shown in Table 1. A graph as shown in FIG. 6 is drawn by taking the maximum inner diameters of the spots as the horizontal axis and the noise of the finished machines assembled with the respective fluorescent wheels as the vertical axis.

TABLE 1

| Fluorescent wheel No. | Maximum inner diameter of the spot (cm) | Noise of the finished machine (dBA) |
|---|---|---|
| 001 | 3.8 | 37.2 |
| 002 | 4.5 | 37.7 |
| 003 | 5.5 | 40 |
| 004 | 6.5 | 43 |
| 005 | 7.6 | 43.1 |
| 006 | 8.4 | 44.2 |
| 007 | 9.5 | 45.3 |
| 008 | 10.6 | 46.2 |
| 009 | 12.5 | 47.8 |
| 010 | 14.2 | 49.2 |

Figure 6:
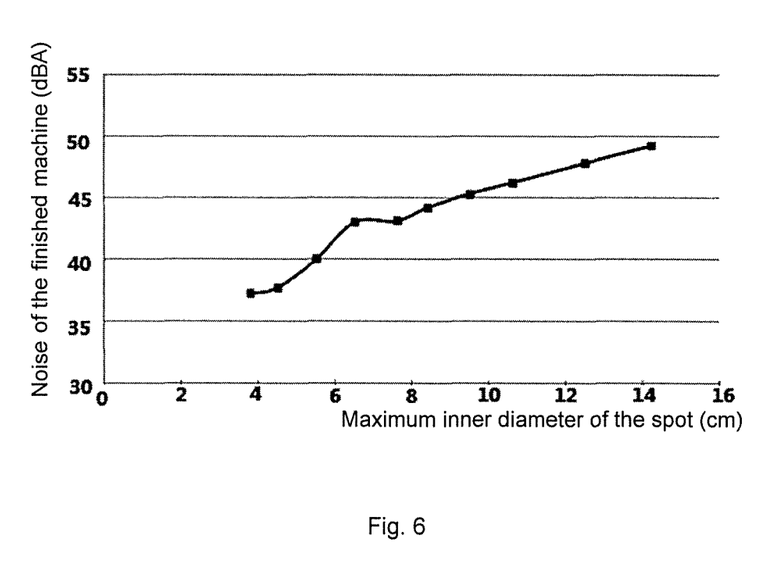
FIG. 6 is a graph showing the relationship between a maximum inner diameter of a spot and noise of a finished machine according to one embodiment of the present disclosure.

From FIG. 6, it can be seen that there is a linear relation between the size of the maximum inner diameter of the spot, which indicates the out-of-flatness and axial run-out of the fluorescent wheel, and the noise of the finished machine. When the detection standard of the noise of the finished machine is 46.2 dBA, the actual maximum inner diameter of the spot corresponding to the fluorescent wheel used is 10.6 cm. In this case, it is only needed to test the maximum inner diameter of the spot of the fluorescent wheel by the method and device provided by the embodiments of the present disclosure. When the maximum inner diameter of the spot is less than or equal to 10.6 cm, it is indicated that the noise generated when the fluorescent wheel is assembled in the finished machine is less than or equal to 46.2 dBA, meeting the noise standard. A fluorescent wheel corresponding to a spot having a maximum inner diameter greater than 10.6 cm is an unqualified product, and the noise of the finished machine assembled with such a fluorescent wheel certainly does not meet the noise standard.

In this way, by screening fluorescent wheels in the early stage of production, fluorescent wheels that enable a finished machine to be qualified in noise are selected to be used for production. During the subsequent production, it is unnecessary to detect the noise of the finished machine so that the production efficiency may be improved. Meanwhile, the produced products are all qualified products meeting the standard and the quality may be ensured.

In the foregoing, in the method and device for detecting flatness of a fluorescent wheel in a laser light source provided by the embodiments of the present disclosure, a laser is adopted to emit laser light which is to be reflected from the wheel surface of the rotating fluorescent wheel; the reflected laser light beam is received by the spot receiving screen and forms an irregular spot on the spot receiving screen; and since the laser light may be irradiated onto the whole circle of the wheel surface of the fluorescent wheel during the rotation of the fluorescent wheel, the irregularity of the spot indicates the out-of-flatness and axial run-out of the fluorescent wheel. Based on this principle, the extent of out-of-flatness of the corresponding fluorescent wheel may be obtained by measuring the inner diameter of the spot. Before fluorescent wheels are assembled in the finished machines, fluorescent wheels which, when assembled in the finished machines, may make the noise of the finished machines higher than the noise standard are screened out. Only fluorescent wheels which may make the finished machines qualified in noise are used for production. During the subsequent production, it is unnecessary to detect the noise of the finished machine, replace the fluorescent wheel for the finished machine unqualified in noise. Hence, the production efficiency may be improved. Meanwhile, the produced products are all qualified products meeting the standard and the quality may be ensured.

Although the preferred embodiments of the present disclosure have been described, other alterations and modifications may occur to those skilled in the art once knowing the basic creative concept. Hence, it is intended to interpret the appended claims as including the preferred embodiments and all alterations and modifications falling into the scope of the present disclosure.

Apparently, for those skilled in the art, various changes and variations may be made to the present disclosure without departing from the spirit and scope of the present disclosure. In this way, if those modifications and variations of the present disclosure belong to the scope defined by the claims of the present disclosure and its equivalences, the present disclosure is intended to encompass those changes and variations.

What is claimed is:

1. A method for detecting flatness of a fluorescent wheel, comprising:
    emitting laser light to a fluorescent wheel by a flatness detection laser;
    acquiring, during the rotation of the fluorescent wheel, a spot of laser light reflected from a substrate of the fluorescent wheel on a spot receiving screen;
    determining an inner diameter of the spot; and
    determining measures of dispersion of the inner diameter of the spot according to the inner diameter of the spot, and determining flatness of the fluorescent wheel according to the measures of dispersion of the inner diameter, wherein a spot having a larger measures of dispersion of the inner diameter shows that its corresponding fluorescent wheel has worse flatness.

2. The method for detecting flatness of the fluorescent wheel according to claim 1, wherein: the measures of dispersion of the inner diameter of the spot comprises a first ratio of a maximum inner diameter to an average inner diameter of the spot,
    determining the maximum inner diameter and the average inner diameter of the spot according to the inner diameter of the spot, and
    determining the flatness of the fluorescent wheel according to the first ratio of the maximum inner diameter to the average inner diameter of the spot.

3. The method for detecting flatness of the fluorescent wheel according to claim 2, wherein said determining flatness of the fluorescent wheel according to the first ratio of the maximum inner diameter to the average inner diameter of the spot specifically comprises:
    judging whether the first ratio of the maximum inner diameter to the average inner diameter of the spot is less than or equal to a first preset ratio;
    if the first ratio of the maximum inner diameter to the average inner diameter of the spot is less than or equal to the first preset ratio, marking said fluorescent wheel as qualified in flatness; and
    if the first ratio of the maximum inner diameter to the average inner diameter of the spot is not less than or equal to the first preset ratio, marking said fluorescent wheel as unqualified in flatness.

4. The method for detecting flatness of the fluorescent wheel according to claim 3, wherein the step of determining said first preset ratio comprises:
    acquiring N spots reflected, during the rotation of N fluorescent wheels, from respective substrates of the N fluorescent wheels, respectively;
    determining N maximum inner diameters and N average inner diameters of the N spots;
    calculating N first ratios of the N maximum inner diameters to the N average inner diameters of the N spots;
    acquiring noise generated by the N fluorescent wheels when assembled in the finished machines respectively; and
    determining said first preset ratio according to an upper limit of allowable noise.

5. The method for detecting flatness of the fluorescent wheel according to claim 1, before acquiring, during the rotation of a fluorescent wheel, the spot of laser light reflected from the substrate of the fluorescent wheel on the spot receiving screen, further comprising:
    controlling an incident angle of laser light emitted by said flatness detection laser to be deviated from a normal line of the substrate and be less than 90°.

6. The method for detecting flatness of the fluorescent wheel according to claim 1, before acquiring, during the rotation of the fluorescent wheel, the spot of laser light reflected from the substrate of the fluorescent wheel on the spot receiving screen, further comprising:
    controlling laser light emitted by said flatness detection laser to be irradiated onto a peripheral region of the substrate of the fluorescent wheel.

7. The method for detecting flatness of the fluorescent wheel according to claim 1, wherein: the measures of dispersion of the inner diameter of the spot comprises a second ratio of the maximum inner diameter to a minimum inner diameter of the spot,
    determining the maximum inner diameter and the minimum inner diameter of the spot according to the inner diameter of the spot, and
    determining the flatness of the fluorescent wheel according to the second ratio of the maximum inner diameter to the minimum inner diameter of the spot.

8. The method for detecting flatness of the fluorescent wheel according to claim 7, wherein said determining flatness of the fluorescent wheel according to the second ratio of the maximum inner diameter to the minimum inner diameter of the spot specifically comprises:
    judging whether the second ratio of the maximum inner diameter to the minimum inner diameter of the spot is less than or equal to a second preset ratio;
    if the second ratio of the maximum inner diameter to the minimum inner diameter of the spot is less than or equal to the second preset ratio, marking said fluorescent wheel as qualified in flatness; and
    if the second ratio of the maximum inner diameter to the minimum inner diameter of the spot is not less than or equal to the second preset ratio, marking said fluorescent wheel as unqualified in flatness.

9. The method for detecting flatness of the fluorescent wheel according to claim 8, wherein the step of determining said second preset ratio comprises:

acquiring N spots reflected, during the rotation of N fluorescent wheels, from respective substrates of the N fluorescent wheels, respectively;

determining N maximum inner diameters and N minimum inner diameters of the N spots;

calculating N second ratios of the N maximum inner diameters to the N minimum inner diameters of the N spots;

acquiring noise generated by the N fluorescent wheels when assembled in the finished machines respectively; and determining said second preset ratio according to an upper limit of allowable noise.

10. A device for detecting flatness of a fluorescent wheel, the device comprising: a fluorescent wheel, a flatness detection laser, a spot receiving screen, a spot acquisition unit and a flatness detection unit, wherein said flatness detection laser is configured to emit laser light which is to be irradiated onto a wheel surface of the fluorescent wheel, said fluorescent wheel is configured to reflect the laser light emitted by said flatness detection laser after receiving the laser light during the rotation, said spot receiving screen is configured to form a spot in its plane after receiving the laser light reflected from the fluorescent wheel, said spot acquisition unit is configured to acquire the spot which is formed by reflecting the laser light emitted by said flatness detection laser onto said spot receiving screen, and said flatness detection unit is configured to analyze an inner diameter of the spot to determine measures of dispersion of the inner diameter, and determine flatness of the fluorescent wheel according to the measures of dispersion of the inner diameter, wherein a spot having a larger maximum measures of dispersion of the inner diameter shows that its corresponding fluorescent wheel has worse flatness.

11. The device for detecting flatness of the fluorescent wheel according to claim 10, wherein the flatness detection unit is specifically configured to determine a maximum inner diameter and an average inner diameter after analyzing the inner diameter of the spot, and determine the flatness of the fluorescent wheel according to a first ratio of the maximum inner diameter to the average inner diameter of the spot;

or, determine the maximum inner diameter and a minimum inner diameter after analyzing the inner diameter of the spot, and determine the flatness of the fluorescent wheel according to a second ratio of the maximum inner diameter to the minimum inner diameter of the spot.

12. The device for detecting flatness of the fluorescent wheel according to claim 10, wherein said flatness detection unit comprises a flatness judgment module and a marking module;

when said flatness detection unit is specifically configured to determine a maximum inner diameter and an average inner diameter after analyzing the inner diameter of the spot, and determine the flatness of the fluorescent wheel according to a first ratio of the maximum inner diameter to the average inner diameter of the spot:

said flatness judgment module is configured to judge whether the first ratio of the maximum inner diameter to the average inner diameter of the spot is less than or equal to a first preset ratio, said marking module is configured to: if the flatness judgment module judges that the first ratio of the maximum inner diameter to the average inner diameter of the spot is less than or equal to the first preset ratio, mark the fluorescent wheel as qualified in flatness, otherwise mark the fluorescent wheel as unqualified in flatness; or when said flatness detection unit is specifically configured to determine the maximum inner diameter and a minimum inner diameter after analyzing the inner diameter of the spot, and determine the flatness of the fluorescent wheel according to a second ratio of the maximum inner diameter to the minimum inner diameter of the spot:

said flatness judgment module is configured to judge whether the second ratio of the maximum inner diameter to the minimum inner diameter of the spot is less than or equal to the second preset ratio, and said marking module is configured to: if the flatness judgment module judges that the second ratio of the maximum inner diameter to the minimum inner diameter of the spot is less than or equal to the second preset ratio, mark the fluorescent wheel as qualified in flatness, otherwise mark the fluorescent wheel as unqualified in flatness.

13. The device for detecting flatness of the fluorescent wheel according to claim 10, wherein said flatness detection laser is a He-Ne laser.

14. The device for detecting flatness of the fluorescent wheel according to claim 10, wherein a front surface or rear surface of the substrate of said fluorescent wheel is a polished surface.

15. The device for detecting flatness of the fluorescent wheel according to claim 10, wherein a front surface or rear surface of the substrate of said fluorescent wheel is coated with a high-reflectivity layer.

16. The device for detecting flatness of the fluorescent wheel according to claim 10, wherein a reflection area of the laser light emitted by the flatness detection laser on the fluorescent wheel substrate is located outside a region having fluorescent powder.

17. A method for detecting flatness of a fluorescent wheel, comprising:

emitting laser light to a fluorescent wheel by a flatness detection laser;

acquiring, during the rotation of the fluorescent wheel, a spot of laser light reflected from a substrate of the fluorescent wheel on a spot receiving screen;

determining an inner diameter of the spot; and determining a maximum inner diameter of the spot according to the inner diameter of the spot, and determining flatness of the fluorescent wheel according to the maximum inner diameter of the spot, wherein a spot having a larger maximum inner diameter shows that its corresponding fluorescent wheel has worse flatness.

18. The method for detecting flatness of the fluorescent wheel according to claim 17, wherein said determining flatness of the fluorescent wheel according to the maximum inner diameter of the spot specifically comprises:

judging whether the maximum inner diameter of the spot is less than or equal to a preset inner diameter value;

if the maximum inner diameter of the spot is less than or equal to the preset inner diameter value, marking said fluorescent wheel as qualified in flatness; and if the maximum inner diameter of the spot is not less than or equal to the preset inner diameter value, marking said fluorescent wheel as unqualified in flatness.

19. The method for detecting flatness of the fluorescent wheel according to claim 18, wherein the step of determining said preset inner diameter value comprises:
  acquiring N spots reflected, during the rotation of N fluorescent wheels, from respective substrates of the N fluorescent wheels, respectively;
  determining N maximum inner diameters of the N spots;
  acquiring noise generated by the N fluorescent wheels when assembled in the finished machines respectively; and
  determining said preset inner diameter value according to an upper limit of allowable noise.

20. A device for detecting flatness of a fluorescent wheel, the device comprising: a fluorescent wheel, a flatness detection laser, a spot receiving screen, a spot acquisition unit and a flatness detection unit, wherein
  said flatness detection laser is configured to emit laser light which is to be irradiated onto a wheel surface of the fluorescent wheel,
  said fluorescent wheel is configured to reflect the laser light emitted by said flatness detection laser after receiving the laser light during the rotation,
  said spot receiving screen is configured to form a spot in its plane after receiving the laser light reflected from the fluorescent wheel,
  said spot acquisition unit is configured to acquire the spot which is formed by reflecting the laser light emitted by said flatness detection laser onto said spot receiving screen, and
  said flatness detection unit is configured to analyze an inner diameter of the spot to determine a maximum inner diameter of the spot, and determine flatness of the fluorescent wheel according to the maximum inner diameter of the spot, wherein a spot having a larger maximum inner diameter shows that its corresponding fluorescent wheel has worse flatness.

21. The device for detecting flatness of the fluorescent wheel according to claim 20, wherein said flatness detection unit comprises a flatness judgment module and a marking module;
  said flatness judgment module is configured to judge whether the maximum inner diameter of the spot is less than or equal to a preset inner diameter value;
  said marking module is configured to: if the flatness judgment module judges that the maximum inner diameter of the spot is less than or equal to the preset inner diameter value, mark the fluorescent wheel as qualified in flatness, otherwise mark the fluorescent wheel as unqualified in flatness.

* * * * *

UNITED STATES PATENT AND TRADEMARK OFFICE
CERTIFICATE OF CORRECTION

PATENT NO. : 10,132,751 B2  
APPLICATION NO. : 15/174407  
DATED : November 20, 2018  
INVENTOR(S) : Fei Zhao et al.

It is certified that error appears in the above-identified patent and that said Letters Patent is hereby corrected as shown below:

On the Title Page

(73) Assignee(s) should read:  
--HISENSE USA CORP., Suwanee, GA (US)--.

Under Other Publications Section should read:  
--Office Action issued in corresponding Chinese Patent Application No. 201510767271.4, dated Aug. 17, 2017.--.

Signed and Sealed this  
Eleventh Day of June, 2019

Andrei Iancu  
*Director of the United States Patent and Trademark Office*